(12) United States Patent
Brock-Fisher

(10) Patent No.: US 6,500,126 B1
(45) Date of Patent: Dec. 31, 2002

(54) ULTRASOUND SYSTEM TRANSDUCER ADAPTER

(75) Inventor: George A. Brock-Fisher, Andover, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/024,761

(22) Filed: Dec. 20, 2001

(51) Int. Cl.$^7$ ................................................ A61B 8/00
(52) U.S. Cl. ...................... 600/459; 600/437; 600/466
(58) Field of Search ............................ 600/437–472; 601/2

(56) References Cited

U.S. PATENT DOCUMENTS 4,957,100 A * 9/1990 Herzog et al. ................. 601/2
5,318,027 A * 6/1994 Fukui ........................... 600/437
5,544,660 A * 8/1996 Crowley ....................... 600/466

* cited by examiner

Primary Examiner—Marvin M. Lateef
Assistant Examiner—Ruby Jain
(74) Attorney, Agent, or Firm—John Vodopia

(57) ABSTRACT

An ultrasound imaging system comprising an ultrasound transducer, an ultrasound imaging device incompatible with the transducer and a transducer adapter including an adapter-transducer connector to connect to a transducer connector of the ultrasound transducer, a system connector to connect to an ultrasound connector of the ultrasound imaging device, and an interface to provide compatible electrical information signals to/from the ultrasound transducer from/to the ultrasound imaging device via the connectors.

20 Claims, 4 Drawing Sheets

ULTRASOUND SYSTEM TRANSDUCER
ADAPTER

BACKGROUND OF THE INVENTION

1. Field of the Invention

The present invention relates to an ultrasound-imaging-device transducer adapter. More particularly, the present invention relates to an apparatus and method to operate ultrasound transducers designed for one ultrasound imaging device with another different ultrasound imaging device.

2. Description of the Related Art

There are currently several manufacturers of medical ultrasound imaging systems. Because there has not been a need or effort at standardization, each distinct manufacturer has a unique configuration for the connector that facilitates the connection of an ultrasound transducer (probe) to the ultrasound imaging system. The ultrasound transducer converts electrical signals into sounds, which are propagated, for example, into a human body and reflected from internal body structures. The reflected sounds are converted back to electrical signals by the transducer and processed by an ultrasound imaging device to image the internal body structures.

A typical ultrasound transducer, such as a phased-array or other array transducer, has many transducer elements (e.g., 64 up to 288 elements) that perform electrical to acoustic and acoustic to electrical conversion. Wires (cable, electrical conductors) connect the transducer elements to a transducer connector. Typically, the wires terminate at pins in the transducer connector. The transducer elements via the transducer connecter transmit and receive electrical signals used for imaging by the ultrasound imaging device.

A typical ultrasound imaging device has an operator control and input interface (e.g., a keyboard), a display device to display information and images, a storage unit to store the information and the images, a communication interface to communicate to external devices and processors executing software that control the ultrasound imaging system components. The communication interface includes at least one system connector that matches and fits transducer connecters to connect transducers to the ultrasound imaging device.

Transducers are optimized for specific applications, thereby having various types/kinds of transducers. For example, one kind of transducer can be optimized for babies or pediatric cases, another one can be optimized for adults, and still another one can be optimized for cardiac or abdominal imaging. The transducers can physically differ, for example, by having different transducer elements and/or different transducer connectors. Typically, a manufacturer has a method of identifying a transducer so that the ultrasound imaging device determines the type of transducer connected to the device and configures appropriate parameters of the device to properly operate the connected transducer (e.g., execute software to operate the identified transducer). The transducer can include a memory unit in a transducer handle to store identification information. The memory unit can be, for example, random access memory (RAM) and/or erasable programmable read only memory (EPROM). The identification information identifies the type of transducer connected to the ultrasound imaging device. The identification information accommodates connecting different type transducers of a manufacturer with the same manufacturer's ultrasound imaging device, allowing for interchangeability of the manufacturer's probes. Therefore, a typical ultrasound imaging device by one manufacturer has more than one system connectors, for example, 3 or 4, to connect and operate more than one optimized transducers of the one manufacturer and the ultrasound imaging device reads transducer identification information from the transducer to configure the device.

However, a transducer from one manufacturer cannot operate with an ultrasound device from other manufacturers, unless the manufacturers cooperate by disclosing/sharing interface (transducer to ultrasound imaging device connection) information. Therefore, there has not been much effort to connect and operate incompatible transducers to/with an ultrasound imaging device. Further, typical transducer adapters have been limited to only providing a physical pass through of electrical signals to accommodate physically incompatible connectors. Because of mergers and acquisitions in the ultrasound industry between manufacturers of ultrasound imaging devices and/or manufacturers of transducers, companies that once competed with each other are now working together in the marketplace. In particular, some companies may have achieved technical superiority/excellence in design of ultrasound imaging devices, while others may have achieved technical superiority in transducer design. Therefore, there is a need to connect and use ultrasound transducers designed for one ultrasound imaging device with another different ultrasound imaging device.

SUMMARY OF THE INVENTION

The present invention can practically and efficiently connect and operate transducers to/with an incompatible ultrasound imaging device. For example, the apparatus of the present invention can connect a transducer from one manufacturer to an ultrasound imaging device of another manufacturer.

The present invention can be attained by an ultrasound transducer adapter that comprises an adapter-transducer connector to connect to a transducer connector of an ultrasound transducer storing identification information, a system connector to connect to an ultrasound imaging device incompatible with the ultrasound transducer, and an interface to read via the adapter-transducer connector the identification information from the ultrasound transducer, to convert the identification information to a compatible configuration information of the ultrasound imaging device and to transmit the compatible configuration information to the ultrasound imaging device via the system connector. The ultrasound imaging device is programmed to operate at least one transducer, each transducer having a registered identification code and the transmitted compatible configuration information is one of the registered identification codes. The ultrasound imaging device uses setting information to operate at least one ultrasound transducer and the transmitted compatible configuration information is the setting information.

Further, the present invention can be attained by an ultrasound transducer adapter that comprises an adapter-transducer connector to connect to a transducer connector of an ultrasound transducer, a system connector to connect to an ultrasound imaging device incompatible with the ultrasound transducer, and an interface to provide compatible electrical information signals to/from the ultrasound transducer from/to the ultrasound imaging device via the connectors of the adapter.

Further, the present invention can be attained by an ultrasound transducer adapter that comprises an adapter-transducer connector to connect to a transducer connector of an ultrasound transducer with transducer elements, a system connector to connect to an ultrasound imaging device with transmitters and receivers, which are incompatible with the transducer elements, to transmit and receive electrical signals to/from the ultrasound transducer, and an interface to provide compatible information signals between the ultrasound transducer and the ultrasound imaging device by mapping the transducer elements from the ultrasound transducer to pins of the system connector according to connection configuration of the ultrasound imaging device and by converting electrical signals of the transducer elements to electrical signals compatible with the transmitters and receivers and/or converting electrical signals from the transmitters and receivers to electrical signals compatible with the transducer elements. The interface converts the electrical signals by matching electrical specifications of the transducer elements to electrical specifications of the transmitters and receivers and vice versa. In particular, the interface converts the electrical signals by transforming/matching impedance of the electrical signals from the transducer elements to impedance of the electrical signals of the transmitters and receivers and/or by transforming/matching the impedance of the electrical signals from the transmitters and receivers to the impedance of the transducer elements.

Further, the present invention can be attained by an ultrasound imaging system and method with an ultrasound transducer adapter of the present invention.

Advantages of the invention will be set forth in part in the description which follows and, in part, will be obvious from the description, or may be learned by practice of the invention.

BRIEF DESCRIPTION OF THE DRAWINGS

The advantages of the invention will become apparent and more readily appreciated from the following description of example embodiments, taken in conjunction with the accompanying drawings of which.

DETAILED DESCRIPTION OF THE PREFERRED EMBODIMENTS

Figure 1:
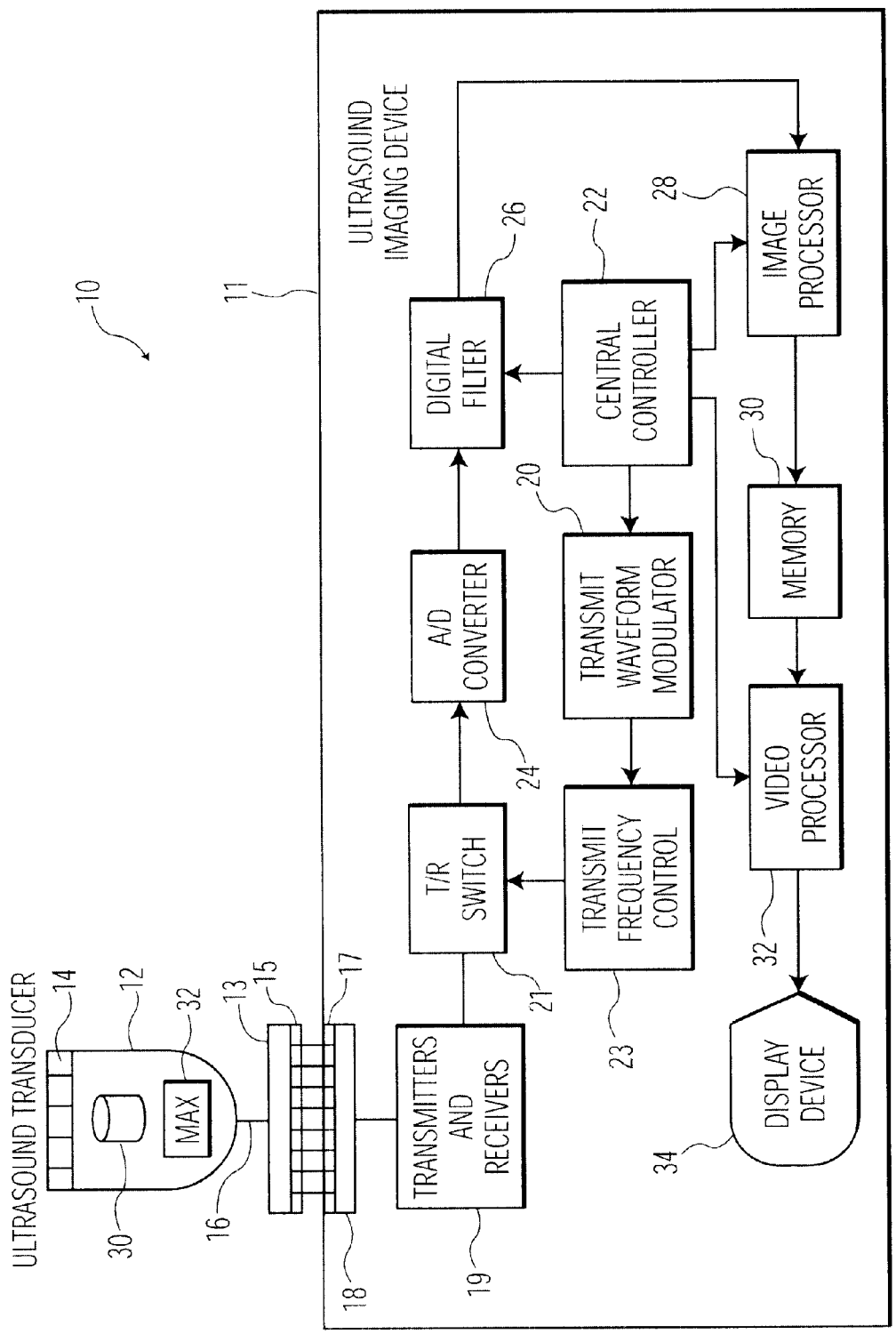
FIG. 1 is a functional block diagram of a conventional ultrasound imaging system.

Reference will now be made in detail to example embodiments of the present invention, which are illustrated in the accompanying drawings, wherein like reference numerals refer to the like elements throughout. The example embodiments are described below to explain the present invention by referring to the figures.

FIG. 1 is a functional block diagram of a typical ultrasound imaging system 10. FIG. 1 does not necessarily illustrate every component of the system, emphasis instead being placed upon the components most relevant to the present invention. The ultrasound imaging system 10 comprises an ultrasound transducer (probe) 12 and an ultrasound imaging device 11. The transducer comprises an array transducer 14 (transducer elements) connected to conductor elements 16, such as conventional wires (a cable) that transmit electrical signals, and a transducer connector 13. Conductor pins 15 are formed at the transducer connector 13. The wires 16 terminate at the pins 15 of the transducer connector 13 to connect to another connector fitting (for example, receiving) the pins 15. The wires 16 electrically connect the transducer elements 14 to the transducer connector 13 to transmit and receive electrical signal to/from the ultrasound imaging device 11 connected to the transducer connector 13. Therefore, the wires 16 and the transducer connector 13 provide a mechanism to connect the transducer 12 to the ultrasound imaging device 11.

The transducer 12 can include a multiplexer (MUX) 32, which is a collection of electronic switches embodied in the form of integrated circuits allowing the transducer 12 to selectively connect a subset of the transducer elements 14 to a set of the pins 15. The ultrasound imaging device 11 can control the MUX 32 to operate the transducer 12 with reduced number of conductors in the cable (wires) 16.

Each transducer element 14 is an ultrasonic transducer converting electricity to sound and converting sound to electricity. The transducer elements 14 convert electrical signals into sounds, which are propagated, for example, into tissue of a human body and reflected from internal body structures. The transducer elements 14 convert the reflected sounds back to electrical signals and the electrical signals are transmitted to the ultrasound imaging device 11 to image the internal body structures.

The transducer 12 further comprises a memory unit 30, such as random access memory (RAM) and/or erasable programmable read only memory (EPROM), to store identification information. The identification information identifies the type of transducer 12 connected to the ultrasound imaging device 11. The identification information accommodates connecting different types of transducers 12 of a manufacturer with the same manufacturer's ultrasound imaging device 11, allowing for interchangeability of the manufacturer's probes.

The ultrasound imaging device (machine/computer) 11 comprises at least one ultrasound connector 18 connected to transmitters and receivers 19 to transmit and receive, respectively, electrical information signals to/from the transducer 12. Conductor pins 17 are formed at the ultrasound connector 18 to connect to another connector fitting (for example, receiving) the pins 17. The pins 15 of the transducer connector 13 match and fit the pins 17 of the ultrasound connector 18 to establish communication between the transducer 12 and the ultrasound imaging device 11. If the connectors 13 and 17 are physically compatible, for example, if the pins 15 and 17 match and fit by having compatible sizes and shapes, the ultrasound imaging device 11 can operate a compatible transducer 12 (e.g., transducer 12 and device 11 built by the same manufacturer) by transmitting and receiving electrical information signals to/from the transducer 12 via the ultrasound connector 18 and the transducer connector 13.

The ultrasound imaging device 11 further comprises a T/R switch 21, which can place the transmitter and receivers 19 in a transmit or receive mode, thereby placing the transducer 12 in a transmit or receive mode. On the transmit side, the ultrasound imaging device 11 comprises a transmit frequency control 23 and a transmit waveform modulator 20 that, under the control of a central controller 22, sets the transmit frequency of the transmit signals and modulates the various transmitted signal lines, respectively.

On the receive side, the ultrasound imaging device 11 includes an A/D converter 24 which converts the analog signals received from the transducer 12 via the T/R switch 21 into digital signals and a digital filter 26 (e.g., an RF filter) that filters signals outside the desired receive band from the received data. In addition, the receive side includes an image processor 28 which processes the output from the digital filter 26. The processed data can be stored in a storage unit 30, such as RAM, EPROM, and, after being processed by a video processor 32, displayed on the display device 34. Therefore, the ultrasound device 11 can image ultrasound echoes received from the body of a patient via the transducer 12. The ultrasound imaging system 10, including various components such as the connectors 13 and 18, can be implemented in software, hardware, or a combination thereof using conventional, commercially available, techniques.

Figure 2:
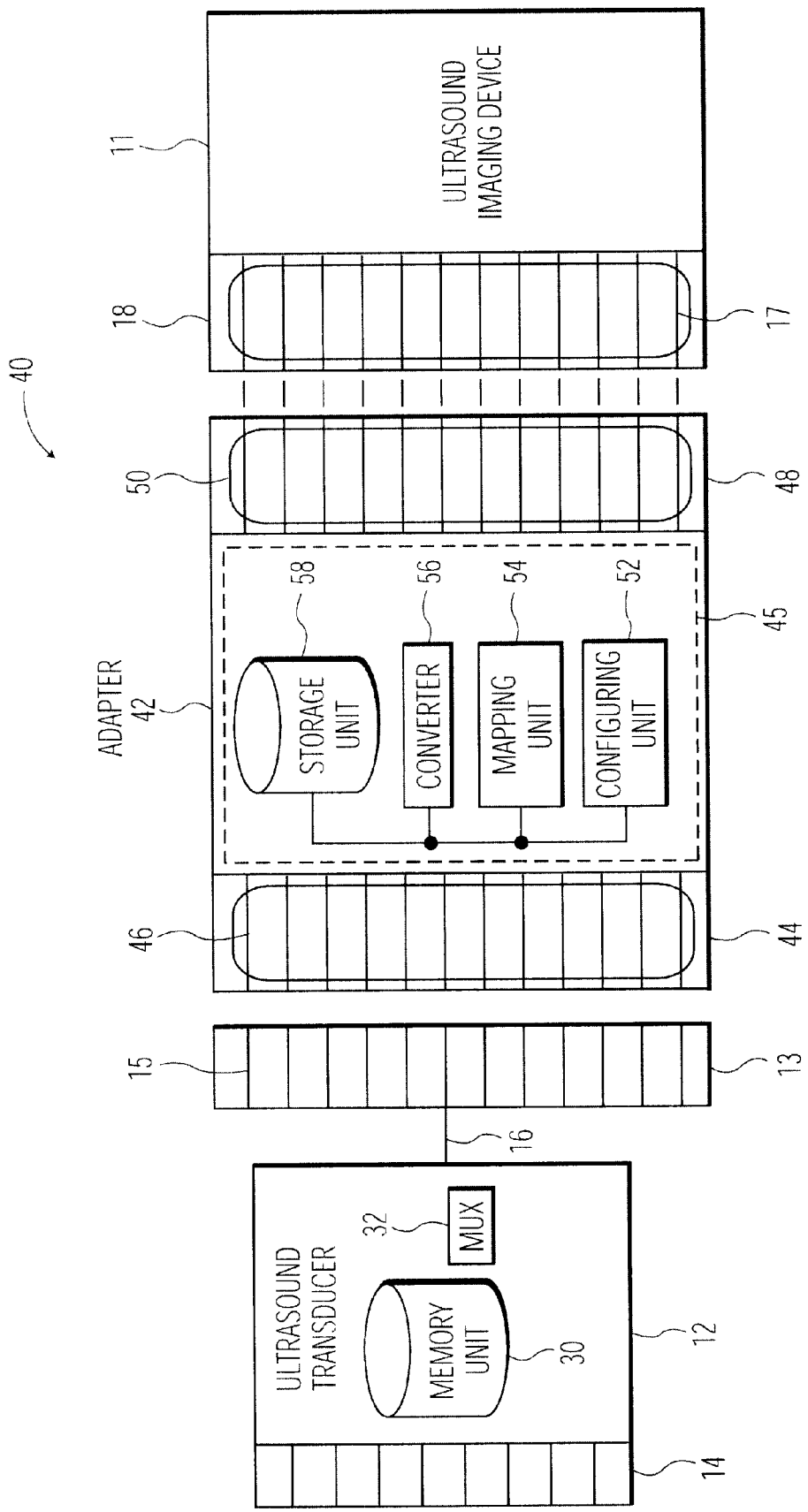
FIG. 2 is a functional block diagram of an ultrasound imaging system according to the present invention.

FIG. 2 is a functional block diagram of an exemplary ultrasound imaging system 40, according to the present invention. The ultrasound imaging system 40 comprises the transducer (probe) 12, the ultrasound imaging device 11 and an ultrasound transducer adapter 42. With the adapter 42, an imaging device designed to operate particular transducers can operate ultrasound transducers designed for other different ultrasound imaging devices. Therefore, the ultrasound device 11 can operate incompatible transducers 12 by using the adapter 42.

The transducer adapter 42 comprises at least one adapter-transducer connector 44, which includes conductor pins 46, to connect to the transducer connector 13. The transducer adapter 42 further comprises at least one system connector 48, which includes conductor pins 50, to connect to the ultrasound connector 18 of the ultrasound device 11. An interface 45 is in communication with the adapter-transducer connector 44 and the system connector 48 to exchange compatible information between the ultrasound device 11 and the transducer 12, which is incompatible with the ultrasound device 11. In particular, a transducer 12 built by one manufacture can connect and communicate with an incompatible ultrasound imaging device 11 built by another manufacturer via the transducer adapter 42. The adapter 42 provides means for connecting an ultrasound transducer incompatible with an ultrasound imaging device.

The two connectors 44 and 48 in an example embodiment of the present invention would be different physical connectors (for example, different types of pins) and provide different connections as far as which pins on one connector connect to which pins on the other connector.

The interface 45 comprises a configuring unit 52, a mapping unit 54, a converter 56 and a storage unit 58. The configuring unit 52, the mapping unit 54 and the converter 56 can be as program segments, thereby being implemented by using processors (not shown) executing software and/or can be implemented using hardware, using conventional techniques. Storage unit 58, such as memory (e.g., RAM, EPROM), hard drives or drives for removable media (e.g., CD-R, CD-ROM, CD-RW, DVD-ROM and DVD-RAM), provides local information storage.

At least one or more of the following information is needed to connect and operate a transducer 12 designed for one particular ultrasound imaging device to/with another different ultrasound imaging device 11. The geometry of the transducer elements 14 may be needed. For example, sizes and shapes of the transducer elements 14 and physical arrangement (e.g., spacing) of the transducer elements 14. Further, information may be needed on how the transducer elements 14 connect/terminate to/at the pins 15 of the transducer connector 13 (i.e., transducer elements 14 interconnections to the pins 15). Further, the MUX 32 configuration may be needed when the transducer 12 uses the MUX 32. Further, the physical geometry of the connectors 13 and 18 may be needed, such as sizes, shapes and types of the pins 15 and 17. Further, the electrical specifications of each transducer element 14 may be needed, such as frequency of operation, response (delay values for transmitters and receivers 19), scan format, bandwidth, sensitivity, ability to convert acoustic energy to electrical energy, electrical impedance, etc. Some electrical specifications can depend on the geometry of the transducer elements, type of connector 13 and/or communication technology used between transducer elements 14 and an ultrasound imaging device 11. Such transducer connection and operation information can be stored in the storage unit 58 of the transducer adapter 42.

Therefore, in an exemplary embodiment of the present invention, the mapping unit 54 can provide a physical mapping (i.e., a physical pass through of electrical signals) between the transducer connector 13 of the transducer 12 and the ultrasound connector 18 of the ultrasound imaging device 11. The mapping unit 54 maps the pins 46 of the adapter-transducer connector 44 to the pins 50 of the system connector 48 according to transducer-connection configuration of the ultrasound imaging device 11. The mapping unit 54 can be embodied in hardware/software using conventional techniques to provide a pass through of electrical signals between the transducer connecter 13 and the ultrasound connector 18 via the adapter 42.

The configuring unit 52 can translate the identification information read from the memory unit 30 of the transducer 12 to an identification information known (recognized) by the ultrasound imaging device 11. The transducer identification information informs an ultrasound imaging device 11 of a transducer type connected to the device 11, so that the device can properly operate the transducer 12 by, for example, recognizing the geometry of the transducer elements 14 and/or configuring the device 11 to electrical specifications compatible with the transducer 12. Therefore, for example, when an ultrasound imaging device 11 is programmed to operate at least one transducer 12, each transducer having a registered identification code, the configuring unit 52 can translate the read identification information of an incompatible transducer to one of the registered identification codes. Further, for example, if the ultrasound imaging device 11 has electrical signal characteristics substantially similar/compatible to/with the transducer 12, advantageously the transducer 12 may be connected to an incompatible ultrasound imaging device 11 and electrical signal conversion by converter 56 (discussed in more detail below) may be obviated with the adapter 42 providing transducer identification translation and properly passing through electrical signals from the transducer 12 to the ultrasound imaging device 11. For example, the ultrasound imaging device 11 and transducer 12 could have substantially different electrical signal characteristics if a geometry of the transducer elements 11 of the transducer 12 are not recognizable/known to the device 11.

Alternatively, the configuring unit 52 can convert the read transducer identification information to a compatible configuration information of the ultrasound imaging device 11 according to transducer-connection configuration information of the device 11 and transmit the compatible configuration information to the ultrasound imaging device 11. The configuration information can be based upon a geometry and/or electrical signal specification information of the transducer elements 14. The configuration information also can include, for example, a unique, or a known (recognized)

transducer identification information. The ultrasound imaging device 11 can receive the transmitted configuration information via the system connector 48 and the ultrasound connector 18 to automatically set (configure) the device 11 to operate the different transducer 12. Therefore, the adapter 42 can automatically provide new or update configuration information of the device 11 to operate different transducers.

In another exemplary embodiment, the converter 56 exchanges compatible information between the transmitters and receivers 19 and the ultrasound transducer 12. In particular, on transmit and/or receive paths formed between the transmitters and receivers 19 and the transducer 12, the converter 56 matches (transforms) the electrical signals mapped by the mapping unit 54 from the transducer elements 14 to electrical signals compatible with the transmitters and receivers 19 of the ultrasound device 11 and/or matches the electrical signals from the transmitter and receivers 19 to electrical signals compatible with the transducer elements 14. Whether the matching is performed on the transmit and/or receive paths can depend on design choice or specific application requirements, although preferably the matching may be performed only on the receive path of the device 11. For example, the matching can be performed on the receive path of the device 11 by matching the electrical specifications of each transducer element 14 with electrical specifications of the transmitters and receivers 19 of the ultrasound imaging device 11. Such electrical specifications include, for example, frequency, response, bandwidth, sensitivity, ability to convert acoustic energy to electrical energy, and electrical impedance, which can be read from storage unit 58 and the matching implemented via hardware and/or software to transmit to the system connector 48 information signals compatible with the transmitters and receivers 19 of the ultrasound imaging device 11. Alternatively, such electrical specification conversion can be implemented via an electrical network (hardware) using conventional techniques.

Figure 3:
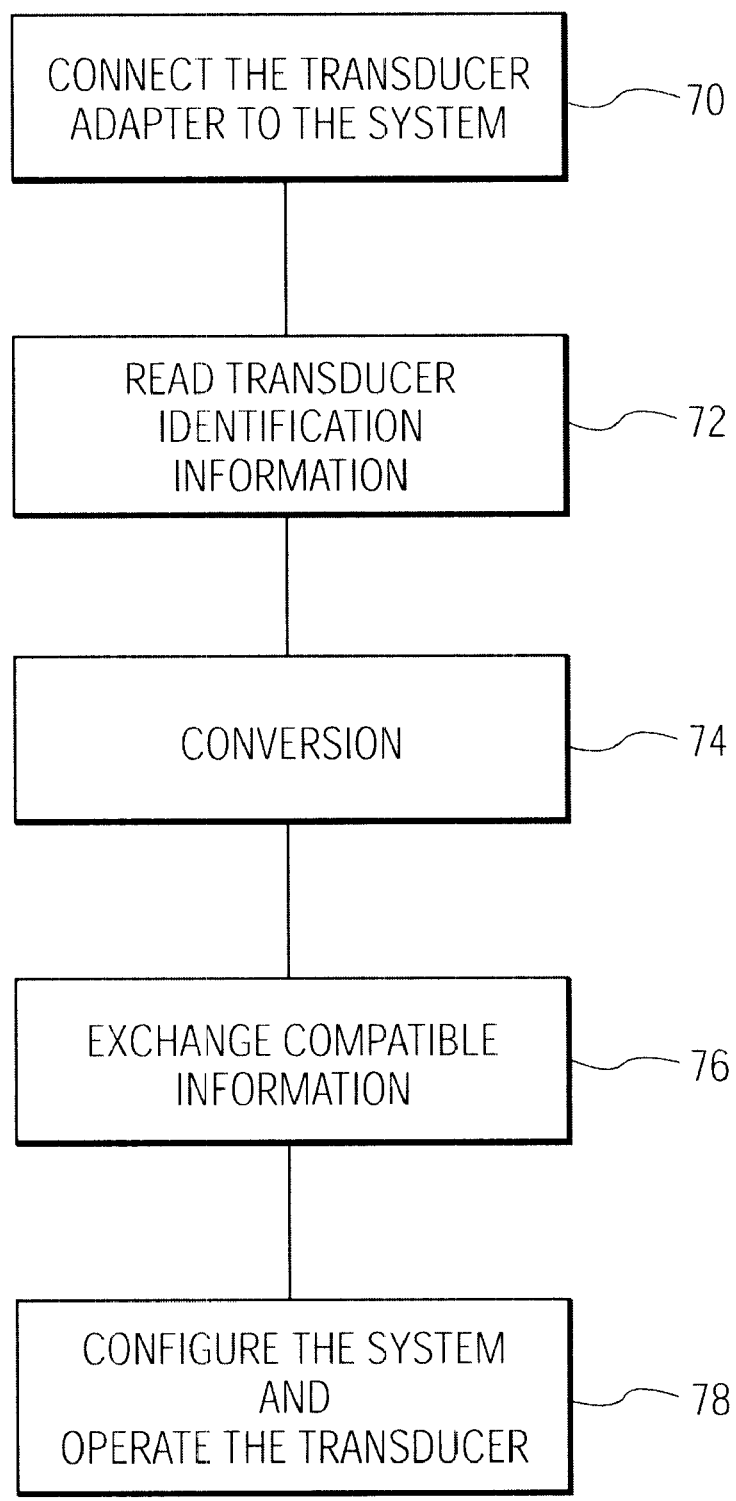
FIG. 3 is an operation flow chart of the ultrasound imaging system according to the present invention.

FIG. 3 is an operation flow chart of an exemplary ultrasound imaging system 40 according to the present invention. At operation 70, the transducer 12, which is not compatible with the ultrasound imaging device 11, is connected to the ultrasound imaging device 11. In particular, the transducer adapter 42 is connected to the transducer 12 by connecting the transducer connector 13 of the transducer 12 to the adapter-transducer connector 44, which match and fit each other. At operation 70, the transducer adapter 42 is also connected to the ultrasound imaging device 11 by connecting the ultrasound connector 18 to the system connector 48 of the adapter 42, which match and fit each other. Next at operation 72, the adapter 42 reads the identification information of the transducer 12, for example, as requested by the ultrasound imaging device 11. In an exemplary embodiment, the identification information can be read from the storage unit 30 in the transducer 12. Next at operation 74, the interface 45, which can include one or more of the configuring unit 52, the mapping unit 54, the converter 56 and the storage unit 58, performs conversion, such as identification information translations and/or converting transducer 12 electrical information signals to ultrasound imaging device 11 compatible electrical information signals and vice versa. For example, at operation 74, on transmit and/or receive paths formed between the transmitters and receivers 19 and the transducer 12, the converter 56 matches (transforms) the electrical signals mapped by the mapping unit 54 from the transducer elements 14 to electrical signals compatible with the transmitters and receivers 19 of the ultrasound device 11 and/or matches the electrical signals from the transmitter and receivers 19 to electrical signals compatible with the transducer elements 14. At operation 76, the adapter 42 exchanges compatible information between the ultrasound transducer 12 and the ultrasound imaging device 11 via the adapter-transducer connector 44 and the system connector 48 of the adapter 42. For example, at operation 76, the adapter 42 transmits the converted information, such as the translated identification information and/or the compatible electrical information signals to the device 11 via the system connector 48. At operation 78, the transmitters and receivers 19 receive the transmitted converted information to configure the ultrasound imaging device 11 and operate the transducer 12 by transmitting and receiving to/from the transducer 12 electrical information signals via the transducer adapter 42.

At operation 74, on the receive path of the device 11 the interface 45 can provide electrical information signals compatible with the ultrasound imaging device 11 via the system connector 48 of the adapter 42 and the ultrasound connector 18 of the device 11, as follows. The interface 45 can translate a transducer identification code read from the transducer 12 to another identification code already known and recognized by the device 11. Further, the interface 45 can transform the electrical specifications of each transducer element 14 with electrical specifications of the transmitters and receivers 19 of the ultrasound imaging device 11. Further, the interface 45 can convert the read transducer identification information to a compatible configuration information of the ultrasound imaging device 11 according to transducer-connection configuration information of the device 11 and to transmit the compatible configuration information to the ultrasound imaging device 11, which configures the device 11 according to the transmitted and received configuration information.

Therefore, the present invention provides an ultrasound imaging system that comprises an ultrasound transducer, at least one ultrasound imaging device incompatible with the transducer and a transducer adapter comprising an adapter-transducer connector to connect to a transducer connector of the ultrasound transducer, at least one system connector to connect to an ultrasound connector of one of the ultrasound imaging devices, and an interface to provide the ultrasound imaging device information compatible with the ultrasound imaging device and to provide the transducer information compatible with the transducer. For example, the transducer adapter 42 can be used to connect a SONOS 5500 (S3 Model) transducer available from Philips Electronics, N.A. Corp. (assignee of the present application), to an HDI 5000 ultrasound device also available from Philips Electronics, N.A. Corp. The SONOS 5500 (S3 Model) transducer is optimized and particularly effective for harmonic imaging and contrast studies and the HDI 5000 has many features good (advantageous) for harmonic imaging and contrast studies. However, the HDI 5000 does not have (cannot operate) a transducer similar to SONOS 5500 (S3 Model) transducer.

Advantageously, according to the present invention, the ultrasound imaging device 11, including hardware and software, need not be modified to connect to incompatible transducers 12, for example, transducers 12 built by manufacturers other than manufacturer of the device 11. However, in some implementations of the present invention, software modification of the ultrasound imaging device 11 may be required. For example, the device 11 software modifications may be required to connect a unique, incompatible or substantially different transducer. Further, for example, the device 11 may include a database of configurations to operate various transducers with incompatible electrical information signals, the database automatically loaded by the adapter 42 with updated and/or new transducer configuration information. The configuration information in the database can also be automatically selected responsive to a transducer identification information translated by the configuring unit 52. The database can be updated using conventional techniques, such as from the adapter 42 or via an external system in communication with the ultrasound imaging device 11.

Although a few example embodiments of the present invention have been shown and described, it would be appreciated by those skilled in the art that changes may be made in the embodiments without departing from the principles and spirit of the invention, the scope of which is defined in the claims and their equivalents.

For example, although the exemplary embodiments describe the wires 16 to electrically connect the transducer elements 14 to the transducer connector 13, which in turn connects to the adapter 42, other conductor elements and/or communication technologies, such as wireless communication technology can be used to exchange information, for example, electrical information signals, between the transducer elements 14 and the adapter 42.

Figure 4:
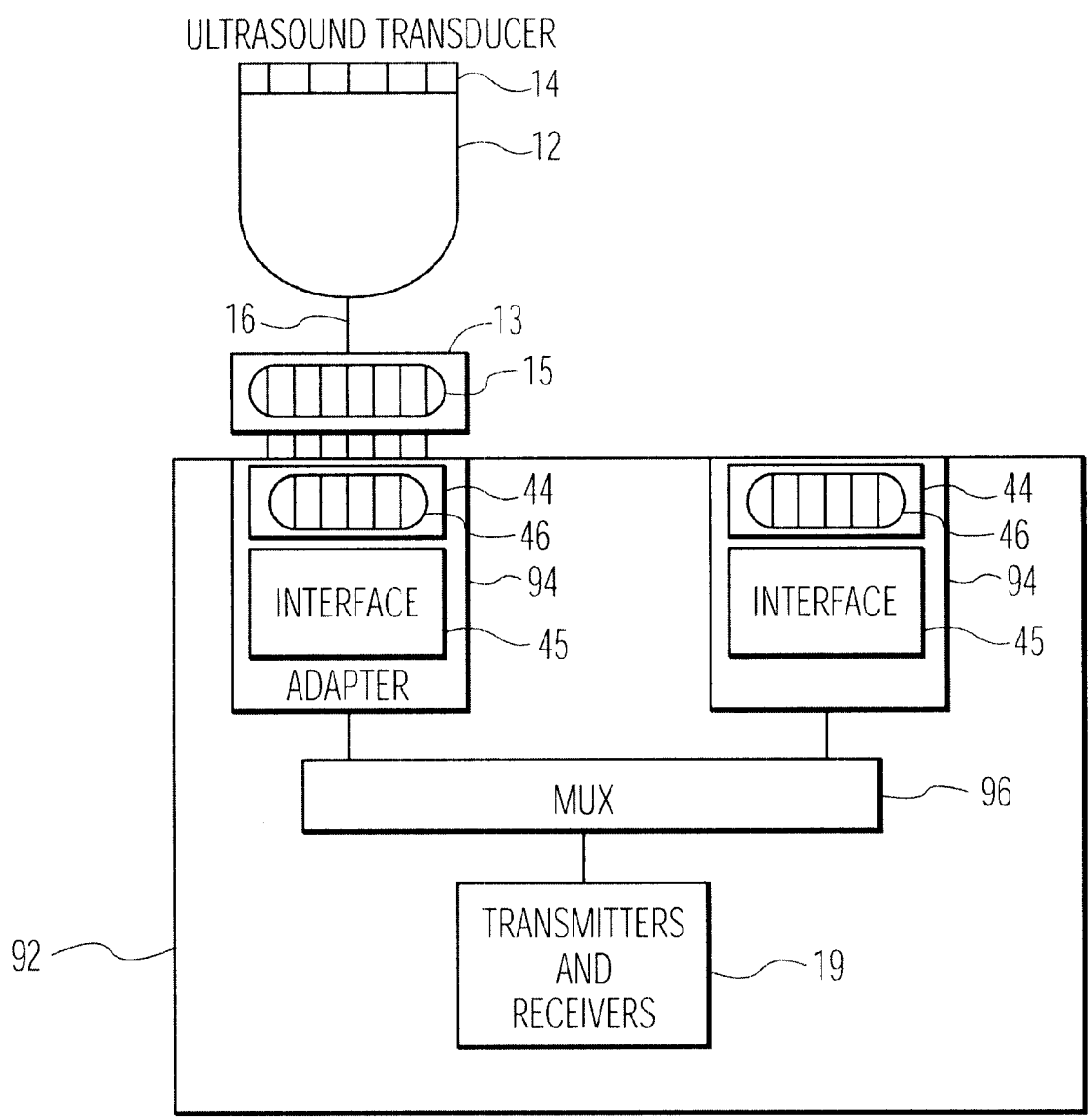
FIG. 4 is a functional block diagram of another exemplary ultrasound imaging system according to the present invention.

FIG. 4 is a functional block diagram of another exemplary ultrasound imaging system 90, according to the present invention. Although the exemplary embodiments describe the adapter 42 being external to the ultrasound imaging device 11, in the system 90 an ultrasound transducer adapter can be integrated with an ultrasound imaging device.

The ultrasound imaging system 90 comprises the ultrasound transducer 12 and an ultrasound imaging device 92, which can operate a transducer 12 being incompatible with the ultrasound imaging device 92. The ultrasound imaging device 92 is a modified ultrasound imaging device 11 incorporating (integrating) at least one ultrasound transducer adapter 94 to connect to at least one incompatible transducer 12.

The integrated ultrasound transducer adapter 94 is a modified ultrasound adapter 42 without the system connector 48. In an exemplary embodiment with one ultrasound transducer adapter 94, the mapping unit 54 may be obviated from the interface 45 and the interface 45 is in communication with the transmitters and receivers 19 to transmit and receive, respectively, electrical information signals. In this embodiment, the integrated transducer adapter 94 can replace the ultrasound connector 18 of the ultrasound imaging device 11. In another embodiment with two or more ultrasound transducer adapters 94, the interface 45 can include the mapping unit 54 and the interface 45 is in communication with a multiplexer 96. The multiplexer 96 is used to connect two or more ultrasound connecters 18 and/or transducer adapters 94 to the transmitters and receivers 19 using conventional techniques. The mapping unit 54 provides a physical mapping between transducer connectors 13 of the transducers 12 and the multiplexer 96.

Further, for example, the transducer adapters 42 and 94 can be configured to provide at least two connectors, thereby providing two or more connectors to connect two or more incompatible transducers and ultrasound imaging devices.

What is claimed is:

1. An ultrasound transducer adapter, comprising:
   an adapter-transducer connector to connect to a transducer connector of an ultrasound transducer storing identification information;
   a system connector to connect to an ultrasound imaging device incompatible with the ultrasound transducer; and
   an interface to read via the adapter-transducer connector the identification information from the ultrasound transducer, to convert the identification information to a compatible configuration information of the ultrasound imaging device and to transmit the compatible configuration information to the ultrasound imaging device via the system connector.

2. The ultrasound transducer adapter of claim 1, wherein the transmitted compatible configuration information is one of identification codes registered in the ultrasound imaging device, the identification codes identifying ultrasound transducers that the ultrasound imaging device is programmed to operate.

3. The ultrasound transducer adapter of claim 2, wherein the transmitted compatible configuration information is setting information used by the imaging device to operate the ultrasound transducers.

4. The ultrasound transducer adapter of claim 3, wherein the configuration information is based upon a geometry and/or electrical signal specification information of transducer elements of the ultrasound transducer.

5. The ultrasound transducer adapter of claim 1, wherein the ultrasound transducer adapter comprises more than one adapter-transducer connectors.

6. An ultrasound transducer adapter, comprising:
   an adapter-transducer connector to connect to a transducer connector of an ultrasound transducer having transducer elements;
   a system connector to connect to an ultrasound imaging device having transmitters and receivers, where the transmitter and receivers are incompatible with the transducer elements, the system connector to transmit and receive electrical signals to/from the ultrasound transducer; and
   an interface to provide compatible information signals between the ultrasound transducer and the ultrasound imaging device by mapping the transducer elements from the ultrasound transducer to pins of the system connector according to connection configuration of the ultrasound imaging device and by converting electrical signals of the transducer elements to electrical signals compatible with the transmitters and receivers and/or converting electrical signals from the transmitters and receivers to electrical signals compatible with the transducer elements.

7. The ultrasound transducer adapter of claim 6, wherein the interface converts the electrical signals by transforming/matching impedance of the electrical signals from the transducer elements to an impedance of the electrical signals of the transmitters and receivers.

8. The ultrasound transducer adapter of claim 6, wherein the interface converts the electrical signals by matching electrical specifications of the transducer elements to electrical specifications of the transmitters and receivers.

9. The ultrasound transducer adapter of claim 6, wherein the ultrasound transducer adapter comprises more than one adapter-transducer connectors.

10. An ultrasound transducer adapter, comprising:
    an adapter-transducer connector to connect to a transducer connector of an ultrasound transducer;
    a system connector to connect to an ultrasound imaging device incompatible with the ultrasound transducer; and
    an interface in communication with the adapter-transducer and the system connector to provide compatible electrical information signals to/from the ultrasound transducer from/to the ultrasound imaging device via the connectors.

11. An ultrasound imaging system, comprising:

an ultrasound transducer;

an ultrasound imaging device incompatible with the ultrasound transducer; and a transducer adapter comprising an adapter-transducer connector to connect to a transducer connector of the ultrasound transducer, a system connector to connect to an ultrasound connector of the ultrasound imaging device, and an interface to provide the ultrasound imaging device, via the system connector, information compatible with the ultrasound imaging device.

12. The ultrasound imaging system of claim 11, wherein the provided information is transducer identification information recognized by the ultrasound imaging device.

13. The ultrasound imaging system of claim 11, wherein the provided information is configuration information to configure the ultrasound imaging device.

14. The ultrasound imaging system of claim 11, wherein the provided information is transducer identification information recognized by the ultrasound imaging device and compatible electrical information signals.

15. The ultrasound imaging system of claim 11, wherein the interface provides the ultrasound transducer, via the adapter-transducer connector, information compatible with the ultrasound transducer.

16. An ultrasound imaging system, comprising:

at least one ultrasound transducer having transducer elements;

an ultrasound imaging device incompatible with the ultrasound transducers and comprising at least one adapter-transducer connector to connect to at least one transducer connector of the ultrasound transducers, transmitters and receivers to transmit and receive electrical information signals to/from the ultrasound transducers, and an interface to exchange compatible information between the transmitters and receivers and the ultrasound transducers via the adapter-transducer connectors.

17. The ultrasound imaging system of claim 16, wherein the interface comprises:

a configuring unit to provide configuration information of the ultrasound transducers to the ultrasound imaging device; and a converter to convert electrical signals of the transducer elements to electrical signals compatible with the transmitters and receivers.

18. The ultrasound imaging system of claim 17, wherein the ultrasound imaging device further comprises a multiplexer to connect two or more of the ultrasound transducers to the transmitters and receivers; and the interface further comprises a mapping unit to map the transducer elements from the ultrasound transducers to the multiplexer according to connection configuration of the ultrasound imaging device.

19. A method to connect an incompatible ultrasound transducer to an ultrasound imaging device, comprising:

connecting a transducer connector of an ultrasound transducer having transducer elements to an adapter-transducer connector;

connecting an ultrasound imaging device having transmitters and receivers, where the transmitter and receivers are incompatible with the transducer elements, to an adapter-system connector to transmit and receive electrical signals to/from the ultrasound transducer;

mapping the transducer elements from the ultrasound transducer to pins of the adapter-system connector according to connection configuration of the ultrasound imaging device;

transmitting configuration information of the ultrasound transducer to the ultrasound imaging device via the adapter-system connector; and converting electrical signals of the transducer elements to electrical signals compatible with the transmitters and receivers and/or converting electrical signals from the transmitters and receivers to electrical signals compatible with the transducer elements.

20. The method of claim 19, wherein the electrical signals are converted by matching electrical specifications of the transducer elements to electrical specifications of the transmitters and receivers.

* * * * *